United States Patent [19]

Folkers et al.

[11] Patent Number: 4,935,491

[45] Date of Patent: Jun. 19, 1990

[54] EFFECTIVE ANTAGONISTS OF THE LUTEINIZING HORMONE RELEASING HORMONE WHICH RELEASE NEGLIGIBLE HISTAMINE

[75] Inventors: Karl Folkers; Anders Ljungqvist; Dong-Mei Feng, all of Austin, Tex.; Cyril Y. Bowers, New Orleans, La.; Pui-Fun L. Tang, Kowloon, Hong Kong; Minoru Kubota, Yotsukaido, Japan

[73] Assignees: Board of Regents, The University of Texas System, Austin, Tex.; The Administrators of the Tulane Educational Fund, New Orleans, La.

[21] Appl. No.: 88,431

[22] Filed: Aug. 24, 1987

[51] Int. Cl.$^5$ .......................... C07K 7/06; C07K 7/20; A61K 37/38

[52] U.S. Cl. ...................................... 530/313; 530/328

[58] Field of Search .................... 530/328, 313; 514/15

[56] References Cited

U.S. PATENT DOCUMENTS

| | | | |
|---|---|---|---|
| 4,504,414 | 3/1985 | Folkers et al. | 530/313 |
| 4,530,920 | 7/1985 | Nestor et al. | |
| 4,801,577 | 1/1989 | Nestor, Jr. et al. | 530/313 |

OTHER PUBLICATIONS

Hocart, S. J. et al., J. Med. Chem., 30(10), pp. 739–743, 1910–1914, Oct. 1987.
Roeske; et al., *Peptides: Structure and Function*, Proceedings of 9th American Peptide Sym., Pierce Chem. Co., Rockford, IL, 561–564, 1986.
Ljungqvist; et al., Biochem. Biophys. Res. Commun., 148, pp. 849–856, 1987.
Folkers; et al., Z. Naturforsch, B: Chem. Sci., 42(1), pp. 101–106, 1987.
Karten, Marvin J., Endocrine Rev., vol. 7, No. 1, 1986, pp. 44–66.
Dutta, Anand S., Drugs of the Future, vol. 13, No. 8, 1988, pp. 761–767.
Phillips, et al., Life SCiences, vol. 43, 1988, pp. 883–888.
Rivier, et al., J. Med. Chem., 1986, 29, 1846–1851.
Karten, et al. (1987), In Vitro Histamine Release with LHRH Analogs.
Bernardi, et al. (1967), *J. Pharm. Pharmac.*, 19:95–101.
Hautklinik, et al., (1958), *Archiv der Pharmazie*, No. 7:330–338.
Fife and Przystas, (1985), J. Am. Chem. Soc., 4:1041–1047.
Prasad, et al., (1976), *Journal of Medicinal Chemistry*, 19:492–495.
Benoiton, (1964), *Canadian Journal of Chemistry*, 42:2043–2047.
Chemical Abstract, (1959), 10B–Aliphatic Compounds, pp. 11237–11238 (U.S. Pat. No. 2,872,484).
Tjoeng, et al., (1975), *Chem. Ber.*, 108:862–874.
Humphries, et al. (1978), *Journal of Medicinal Chemistry*, 21:120–123.

Primary Examiner—Howard E. Schain
Assistant Examiner—Susan M. Perkins
Attorney, Agent, or Firm—Arnold, White & Durkee

[57] ABSTRACT

The objective of the research was the achievement of antagonists of the luteinizing hormone releasing hormone (LHRH) which would have adequate antagonistic activity to prevent ovulation, and yet would not have a pronounced structural feature to release a histamine, in vivo. Some existing antagonists of LHRH produced edema of the face and extremities in rats. This recent recognition of the edematogenic and anaphylactoid activities of an antagonist of LHRH necessitated new structural changes if such antagonists were to be considered for potential use as contraceptive agents in the human. Consequently, 57 peptides have been designed, synthesized and bioassayed toward achieving a potent antagonist which releases negligible histamine. Since there was no predictable structural sequence which offered assurance of such achievement, it was necessary to design, synthesize and bioassay a very large number of peptides having diverse structural changes toward ultimately discovering an antagonist with the necessary potency of antiovulatory activity and the necessary negligible release of histamine. Ultimately, this objective was achieved, and this application describes the diverse and unpredictable many positive steps which finally led to the objectives.

6 Claims, No Drawings

EFFECTIVE ANTAGONISTS OF THE LUTEINIZING HORMONE RELEASING HORMONE WHICH RELEASE NEGLIGIBLE HISTAMINE

BACKGROUND OF THE INVENTION

This invention is on the design, synthesis and bioassay of synthetic analogs of the luteinizing hormone releasing hormone (LHRH). The ultimate achievement was of analogs which function as antagonists of LHRH and which are adequately potent to inhibit ovulation, and have altered structural features which allow the release of only negligible amounts of histamine. Since there is no predictable synthetic approach to an antagonist of high potency and very low histamine release, it was necessary to explore diverse approaches to the objective in order to discover an approach to a combination of structural features which would yield an antagonist of high potency to inhibit ovulation and of very low activity of release histamine.

HISTAMINE RELEASE AS A SERIOUS SIDE EFFECT

Various peptides including substance P, vasoactive intestinal peptide, gastrin, somatostatin, etc., are well known to cause the release of histamine from mast cells. These cells are in many tissues, such as skin, lung and mesentery, gingiva, etc. These cells have granules which contain the histamine and other mediators of inflammation which can be released by peptides and cause dilation of capillaries and increased vascular permeability. When it becomes known that an antagonist of LHRH, [Ac-D-2-Nal$^1$, D-4-F-Phe$^2$, D-Trp$^3$, D-Arg$^6$]-LHRH, caused edema of the face and extremities when it was administered to rats, it became strikingly apparent that such antagonists if administered to human subjects as a contraceptive agent and caused serious edema of the face and elsewhere in the human body, such side effect could soon prevent the administration of such antagonists to human subjects.

The histamine-containing leukocyte is the basophile which can also release histamine by many of the same peptides. Basophiles biochemically differ from mast cells, and such differences may allow for both predictable and unpredictable histamine release in response to antagonists of LHRH. In other words, an antagonist of LHRH, to be used clinically to prevent ovulation, must not significantly release histamine from either the mast cell or the basophile.

The discovery of the side effects which are the edematogenic and anaphylactoid actions from an antagonist of LHRH made mandatory the discovery of new antagonists which prevented ovulation but did not release significant histamine. The side effects have been observed in rats, and it is evident that the Food and Drug Administration would not allow the testing of such antagonists in human subjects which caused such highly undesirable side effects, in rats. It is predictable that such antagonists would produce these side effects in human subjects if they were to be tested.

PRIOR KNOWLEDGE ON PEPTIDE STRUCTURE FOR HISTAMINE RELEASE

Karten et al., in *LHRH and its Analogs: Contraceptive and Therapeutic Applications, Part II*, MTP Press Limited, Lancaster, 1987 (in press), has reviewed available knowledge on the structural characteristics for potent histamine release by antagonists of LHRH. Some of the most important findings are as follows. The most potent LHRH antagonist in triggering histamine release in vitro involves a combination of strongly basic D-amino acid side chains (Arg or Lys) at position 6 and in close proximity to Arg$^8$, and a cluster of hydrophobic aromatic amino acids at the N-terminus. Thus, there is no specific amino acid of the ten amino acids which is solely responsible for histamine release. On the contrary, structural features ranging from the N-terminus (the amino acids in the first few positions, 1-4, etc.), and basic amino acids toward the C-terminus (positions 6 and 8) somehow participate. Even D-Ala in position 10 has some influence on histamine release, which is unclear. By themselves, two basic side chains in close proximity, as in positions 6 and 8, are insufficient to impart high release of histamine, and the cluster of hydrophobic amino acids at the N-terminus is sufficient for high release of histamine. Even a hexapeptide fragment has revealed moderate histamine releasing potency.

There seems to be no correlation between antiovulatory potency and histamine release of these antagonists, in vitro.

In perspective, much of the entire chain of the peptide of ten amino acids may have some influence on histamine release, and the same perspective appears to be true, but to different degrees for high antiovulatory activity.

THE DIFFICULTIES TO SURMOUNT FOR DISCOVERY OF AN ANTAGONIST WITH HIGH POTENCY FOR ANTI-OVULATORY RELEASE AND INSIGNIFICANT RELEASE OF HISTAMINE

These antagonists almost always have ten amino acids in the chain so that one can say that there are ten variables to adjust for anti-ovulatory activity and ten variables to adjust for eliminating histamine release. Then, there are variables for each of the twenty variables, and the number of possible peptides to design, synthesize and assay becomes incalculable. Presumably, some of the ten variables may be independent for anti-ovulatory activity and histamine release, and some variables may overlap for the two biological activities. This situation poses extraordinary difficulties to solve if an antagonist of high potency for anti-ovulation and very low potency for histamine release can be achieved.

Experimentally, all one could do was to explore very diverse structural changes among the ten amino acids, and run assays of both anti-ovulation and histamine release and hope that a potent antagonist essentially free of side effects would be discovered. It was also apparent that new amino acids would have to be synthesized to introduce into the peptide chains, because likely, the commonly available amino acids would not suffice.

SUMMARY OF THE INVENTION

In this invention, arginine and its derivatives were eliminated from the sequences. Lysine was converted into derivatives with acyl groups and with alkyl groups on the ε-amino group, and the amino acid ornithine was acylated and alkylated on the δ-amino group. Both the L- and D-forms of lysine and the L-form of ornithine were used in synthesizing these acyl and alkyl derivatives. Structurally related intermediates were also synthesized. All together, (57) new peptides were synthesized by the basic and minimal concepts of ten variables for anti-ovulation activity and ten variables for histamine release, which may be independent or partially overlapping. On such a basis, the number of such peptides that can be designed becomes overwhelming, and every reasonable priority must be considered to reduce the number of peptides to be synthesized in the hope that a discovery will be realized. Ultimately, two peptides were discovered, as follows.

[N-Ac-D-2-Nal$^1$, D-pClPhe$^2$, D-3-Pal$^3$, NicLys$^5$, D-NicLys$^6$, ILys$^8$, D-Ala$^{10}$]-LHRH was effective to prevent ovulation and released remarkably little histamine.

[N-Ac-D-2-Nal$^1$, D-pClPhe$^2$, D-3-Pal$^3$, PicLys$^5$, D-PicLys$^6$, ILys$^8$, D-Ala$^{10}$]-LHRH was twice as effective as the above peptide, and released no more histamine than do "super agonists", of LHRH, which are presently being marketed by several pharmaceutical companies.

These two new peptides, and related peptides in the table, provide an acceptable balance of high anti-ovulatory activity and low histamine release for full potential clinical utility, but before such utility can be tested, large quantities of the peptides must be synthesized, safety testing conducted, and an IND from the F&DA must be obtained.

DESCRIPTIONS OF PREFERRED EMBODIMENTS

Abbreviations and formulas

BOC: t-butoxycarbonyl
Br-Z: o-bromobenzyloxycarbonyl
nBuOAc: n-butylacetate
n-BuOH: n-butanol
CDCl$_3$: deuterochloroform
CHCl$_3$: chloroform
CH$_2$Cl$_2$: dichloromethane
CH$_3$CN: acetonitril
Cl-Z: o-chlorobenzyloxycarbonyl
DCC: dicyclohexylcarbodiimide
DIEA: diisopropylethylamine
DMF: dimethylformamide
EtOAc: ethyl acetate
EtOH: ethanol
Et$_2$O: diethyl ether
HF: hydrogen fluoride
HOAc: acetic acid
KH$_2$PO$_4$: potassium dihydrogen phosphate
MeOH: methanol
MgSO$_4$: magnesium sulfate
NH$_4$OAc: ammonium acetate
iPrOH: 2-propanol
py: pyridine
TFA: trifluoroacetic acid
THF: tetrahydrofuran
TOS: p-toluensulfonyl
Z: benzyloxycarbonyl The abbreviatons for the unnatural amino acids are in Table I.

Most natural amino acids were obtained from Peninsula Laboratories, San Carlos, CA. The hydroxyl group of Ser was protected as the benzyl ether, the phenolic hydroxyl group of Tyr as the Br-Z derivative, and ε-amino group of Lys as the Cl-Z derivative, the guanidino group of Arg and the imidazole group of Mis as the TOS derivatives. The α-amino function was proteced as the BOC derivative, BOC-Orn(Z) was obtained from Sigma Chemical Co., St. Louis, Mo. BOC-D-2-Nal, BOC-D-3-Pal, BOC-D-Cl$_2$Phe, BOC-pClPhe and BOC-ILys(Z) dicyclohexylamine salt were provided by the Southwest Foundation for Biomedical Research, San Antonio, TX. The benzhydrylamine hydrochloride resin was obtained from Beckman Bioproducts, Palo Alto, CA. The nitrogen content was about 0.65 mmoles/g. The CH$_2$Cl$_2$ was distilled before use.

SYNTHESIS OF INTERMEDIATES

Melting points are uncorrected. NMR data are reported as δ-values downfield from TMS.

Before acylation, the Z and Cl-Z groups of Lys and Orn were cleaved by hydrogenolysis in MeOH in the presence of 10% Pd/C.

BOC-D-BzLys was synthesized by acylation of BOC-D-Lys with benzoyl chloride as described for the L-isomer by Bernardi et al., *J. Pharm. Pharmacol.* 19, 95 (1967).

BOC-DMG-Lys was prepared by acylation of BOC-Lys with chloroacetyl chloride using the same method and the reacting the crude product from 10 mmoles BOC-Lys in 10 ml THF with 10 ml 40% aq. dimethylamine. The reaction mixture was stirred 15 min in ice bath and then 2.5 h at room temperature. After evaporation in vacuo the crude product was dissolved in 10 ml H$_2$O and applied on a Bio-Rad AG1-X8 column, acetate form, 1×25 cm. The column was first washed with 200 ml water and then the product was eluted with 6% HOAc and lyophilized several times to remove the HOAc. Yield 60-70%. Amorphous mass. R$_f$(n-BuOH:py:HOAc:H$_2$O=30:10:3:12)=0.27. Purity >95%. NMR (CDCl$_3$): 1.45, s, 9H, t-butoxy group; 1.85-1.48, m, 6H, β, γ, δ, CH$_2$ groups: 2.6, s, 6H, N(CH$_3$)$_2$; 3.25, m, 2H, ε-CH$_2$; 3.37, s, 2H, N-CH$_2$-CO; 4.15, m, 1H, α-CH.

The other acylated Lys derivatives in Table I were prepared from BOC-D or L-Lys and the corresponding p-nitrophenyl ester.

pNitrophenyl nicotinate. To 9.85 g, 80 mmoles, nicotinic acid and 13.35 g, 96 mmoles p-nitrophenol in 250 ml DMF was added 16.5 g, 80 mmoles DCC with stirring in ice-bath. After 1 h at 0° C. and 3 h at room temperature the urea was filtered off and the product was precipitated by the addition of an equal volume of water. Filtration, drying in vacuo and recrystallization from i-PrOH gave 11.22 g, 57% of white needles. M.p. 172.5°-173° C., m.p. (H. Zinner and H. Fiedler, *Arch. Pharm.* 291(63), 330 (1958)) 172° C.

In the same manner was prepared p-nitrophenyl isonicotinate, 12 g, 61%, m.p. 139°-141° C., m.p. (T. H. Fife and T. J. Przystas, *J. Am. Chem. Soc.* 107, 1041 (1985)) 137°-139° C.

Also in the same way as prepared p-nitrophenyl 6-methylnicotinate. Yield from 70 mmoles 6-methylnicotinic acid: 6.0 g, 33% after recrystallization from MeOH. M.p. 156°-157° C. R$_f$ (2% MeOH in CHCl$_3$)=0.57. NMR (CDCl$_3$): 2.7, s, 3H, CH$_3$; 7.36, d, 1H, py H$^5$; 7.45, m, 2H, H adjacent to the oxygen in the phenyl ring; 8.34, m, 3H, H adjacent to the NO$_2$ group in the phenyl ring overlapping with py H$^4$; 9.27, d, 1H, py H$^2$.

p-nitrophenyl picolinate. 4.92 g, 40 mmoles, picolinic acid and 5.84 g, 42 mmoles p-nitrophenol were suspended/dissolved in 200 ml CH$_2$Cl$_2$. Then 8.24 g, 40 mmoles, DCC was added in 20 ml CH$_2$Cl$_2$ with vigorous stirring. Stirring was continued in room temperature for 17 h. Then the mixture was filtered and the filter cake washed with 30-40 ml $CH_2Cl_2$. The raw product was first treated with 100 ml $Et_2O$ with stirring in ice-bath and filtered. Recrystallization from 250 ml iPrOH gave 6.24 g, 63% product. M.p. 154°-6° C. (dec.). M.p. (Fife and Przystas, loc. cit.) 145°-7° C. Anal. C,H,N,O.

Pyrazinecarboxylic acid p-nitrophenylester. This compound was prepared using the same method as the previous compound. From 40 mmoles pyrazinecarboxylic acid and 44 mmoles p-nitrophenol was obtained 35.2 mmoles, 88%, ester. M.p. 180°-182° C. (dec.). $R_f$ ($CHCl_3$:MeOH=49:1)=0.72. NMR ($CDCl_3$): 7.5, m and 8.37 m, 2H each, hydrogens adjacent to the oxygen and nitro group respectively in the phenol ring; 8.84, m, 1H, pyrazine $H^5$; 8.9, d, 1H, pyrazine $H^6$; 9.48, d, 1H, pyrazine $H^3$.

BOC-NicLys. 2.5 g BOC-Lys (L or D) was suspended in 200 ml DMF with stirring. Then 1.1 equivalent of p-nitrophenyl nicotinate was added and the mixture stirred at room temperature for 36 h. The mixture was then filtered and the filtrate evaporated to dryness at reduced pressure to yield a yellow oil. The residue was stirred with 2×50 ml $Et_2O$ in ice-bath. The first $Et_2O$ phase was decanted, the second was filtered off. Recrystallization from EtOAc/hexanes gave 2.05 g product, 58% (L-form). M.p. 138° C., lit. (Bernardi et al. loc. cit.) 138°-141° C. L-form $[\alpha]^{20}_D = -2.91°$ (MeOH), D-form $[\alpha]^{20}_D = 3.35°$ (MeOH).

L- and D-BOC-INicLys were prepared similarly by acylating 10 mmoles L or D BOC-Lys with p-nitrophenyl isonicotinate in 100 ml DMF, 40 h, room temperature. The crude product was partitioned between 120 ml EtOAc and 50 ml $H_2O$. The EtOAc phase was extracted with 2×50 ml $H_2O$ and 50 ml brine. The original aqueous phase was back-extracted with 30 ml EtOAc. The combined EtOAc phases were then dried ($MgSO_4$) and evaporated and the residue was treated with $Et_2O$ and recrystallized as above to give 1.07 g, BOC-L-INicLys, 30.5%. The yield for the D compound was 1.26 g, 36%. NMR (Acetone $d_6$): 1.4, s, 9H, t-butoxy group; 1.8-1.48, m, 6H, $\beta$, $\gamma$, $\delta$-$CH_2$-; 3.44, t, 2H, $\epsilon$-$CH_2$; 4.13, m, 1H, $\alpha$-CH; 7.77, m, 2H, py $H^5$ and $H^3$; 8.70, m, 2H, py $H^2$ and $H^6$.

L- and D-DOC-PicLys. 1.23 g, 5 mmoles, of L- or D-BOC-Lys was stirred with 1.34 g, 5.5 mmoles, p-nitrophenyl picolinate in 60 ml DMF for 16 h. After filtration and evaporation the product was purified by column chromatography on silica gel on a 4.5×32 cm column and the solvent system n-BuOH:py:HOAc:$H_2O$=30:10:3:12. The product after chromatography was dissolved in EtOAc and washed with $H_2O$, brine, dried and evaporated in vacuo. The yields were usually 60-70%. NMR ($CDCl_3$): 1.43, s, 9H, t-butoxy group; 1.73-1.45, m, 6H, $\beta$, $\gamma$, $\delta$-$CH_2$; 3.47, m, 2H, $\epsilon$-$CH_2$; 4.32, m, 1H, $\alpha$-CH; 7.43, m, 1H, py $H^5$; 7.85, m, 1H, py $H^4$; 8.2, m, 1H, py $H^3$; 8.55, m, 1H, py $H^6$.

L- and D-BOC-MNicLys. 10 mmoles BOC-Lys and 10.5 mmoles p-nitrophenyl 6-methylnicotinate were allowed to react in 150 ml DMF in the usual manner. After 27 h filtration and evaporation yielded a yellow oil. $Et_2O$ treatment (2×50 ml) gave 3.3 g product which was recrystallized from 50 ml 20% MeOH in EtOAc/hexane. yield 2.87 g, 78.6% (L-form). $R_f$(n-BuOH:py:HOAc:$H_2O$=32:10:3:12)=0.61. NMR ($CDCl_3$): 1.46, s, 9H, t-butoxy group; 1.9-1.5, m, 6H, $\beta$, $\gamma$, $\delta$-$CH_2$; 2.57, s, 3H, py $CH_3$; 3.36, m, 2H, $\epsilon$-$CH_2$; 4.11, m, 1H, $\alpha$-CH; 7.22, d, 1H, py $H^5$; 8.08, m, 1H, py $H^4$; 8.95, broad s, 1H, py $H^2$.

L- and D-BOC-PzcLys. Using the method above was obtained from 7.7 moles pyrazine carboxylic acid p-nitrophenyl ester and 7 mmoles BOC-Lys, L or D, in 100 ml DMF about 6 mmoles product after recrystallization from iPrOH. $R_f$(n-BuOH:py:HOAc:$H_2O$=30:10:3:12)=0.47. NMR($CDCl_3$): 1.45, s, 9H, t-butoxy group; 1.9-1.48, m, 6H, $\beta$, $\gamma$, $\delta$-$CH_2$; 3.51, m, 2H, $\epsilon$-$CH_2$; 4.29, m, 1H, $\alpha$-CH; 8.52, q, 1H, pyrazine $H^5$; 8.77, d, 1H, pyrazine $H^6$; 9.41, d, 1H, pyrazine $H^3$.

BOC-L-NicOrn. This compound was prepared the usual way by reacting 7 mmoles p-nitrophenyl nicotinate with 5 mmoles BOC-Orn in 75 ml DMF for 36 h. Evaporation and recrystallization from EtOAc gave 3.5 mmoles, 70%, NicOrn, m.p. 143°-144° C. $R_f$(n-BuOH:HOAc:$H_2O$=4:1:2)=0.70. NMR($CDCl_3$): 1.45, s, 9H, t-butoxy group; 7.46, m, 1H, py $H^5$; 8.27, m, 1H, py $H^4$; 8.69, m, 1H, py $H^6$; 9.05, m, 1H, py $H^2$.

BOC-D-trans-NACAla. 1.43 g, 5 mmoles, BOC-D-trans-3(4-aminocyclohexyl) alanine (provided by the Southwest Foundation for Biomedical Research) was stirred with 1.35 g, 5.5 mmoles, p-nitrophenyl nicotinate in 60 ml DMF for 120 h in room temperature. The mixture was then filtered, evaporated, treated with $Et_2O$ in ice bath and filtered again. Recrystallization was done by heating in 12 ml EtOH and adding 18 ml hot $H_2O$. This produced a clear solution from which crystals separated on cooling. This procedure was repeated twice. Yield: 0.98 g, 50%. Purity >95%. M.p. >220° C. NMR(DMSO $d_6$): 1.46, s, 9H, t-butoxy group; 1.9-1.48, m, 11H, ring $CH_2$, ring CH in position 1 and $\beta$-$CH_2$; 3.72, m, 1H, ring CH in position 4; 3.95, m, 1H, $\alpha$-CH; 7.48, m, 1H, py $H^5$; 8.16, m, 1H, py $H^4$; 8.67, m, 1H, py $H^6$; 8.96, m, 1H, py $H^2$.

BOC-D-cis-NACAla. 5 mmoles BOC-D-cis-3(4-aminocyclohexyl)alanine (source: as above) and 5.5 mmoles p-nitrophenyl nicotinate were allowed to react in DMF as above. Reaction time: 25 h. Purification was achieved by $Et_2O$ treatment as above and silica gel chromatography on a 4.5×32 cm column using the solvent system $CHCl_3$:MeOH:py:HOAc=75:10:10:5. Yield 1.3 g, 61%, amorphous powder. $R_f$ (column system)=0.58. NMR ($CDCl_3$): 1.44, s, 9H, t-butoxy group; 1.95-1.45, m, 11H, ring $CH_2$, ring CH in position 1 and $\beta$-$CH_2$; 4.22, m, 1H, $\alpha$-CH; 4.35, m, 1H, ring CH in position 4: 735, 8.24, 8.63 and 8.98, 1H each, assignments as previous compound.

BOC-IOrn(Z). This compound was prepared from BOC-Orn(Z) by reductive alkylation with acetone and $H_2$/Pd as described by Prasad et al., J. Med. Chem. 19, 492 (1976), followed by conversion to the $N^\delta$-Z derivative with benzyl chloroformate in aqueous alkali (Schotten-Baumann conditions). Purification was achieved by chromatography on silica gel with $CHCl_3$/MeOH 85:15. $R_f$ ($CHCl_3$; MeOH: HOAc=85:15:3)=0.8. NMR($CHCl_3$): 1.10, d, 6H, isopropyl $CH_3$; 1.40, s, 9H, t-butoxy group; 1.7-1.5, m, 4H, $\beta$, $\gamma$-$CH_2$; 3.09, m, 2H, $\delta$-$CH_2$; 4.2, m, 1H, $\alpha$-CH; 5.10, s, 2H, benzyl $CH_2$; 7.3, m, 5H, aromatics.

BOC-CypLys(Z). 2.04 g BOC-Lys(Z) was dissolved in 8 ml of cyclopentanone and 32 ml $H_2O$ containing 0.22 g NaOH. Hydrogenation was performed in the presence of 0.4 g 10% Pd/C at 50-60 psi in a Parr apparatus. After 4 h the hydrogenation was interrupted and 2 ml 0.5M NaOH and 10 ml MeOH were added. The hydrogenation was then continued for 16 h at 50-60 psi. Then filtration and evaporation. The residue was dissolved in 75 ml $H_2O$ and the aqueous phase extracted with three times with $Et_2O$ and once with hexane. The pH was then brought to 6-7 with HCl and the solution evaporated in rotary evaporator, bath temperature 40° C. The resulting product was then converted to the Z-derivative using benzyl chloroformate in aqueous NaOH (Schotten-Baumann conditions). Yield: 1.3 g, 58% overall. $R_f$ (n-BuOH:py:HOAc:H$_2$O-30:10:3:12)=0.69. Purity >95%. NMR (CDCl$_3$): 1.45, s, 9H, t-butoxy groups; 1.95-1.35, m, 14H, ring CH$_2$+$\beta$, $\gamma$, $\delta$-CH$_2$; 3.13, broad t, 2H, $\epsilon$-CH$_2$; 4.34-4.05, m, 2H, $\alpha$-CH+ring CH; 5.13, s, 2H, benzyl CH$_2$; 7.35, m, 5H, aromatic protons.

BOC-Me$_2$Lys, D- and L-. These compounds were prepared by hydrogenolysis of the corresponding Z- or Cl-Z- derivatives in the presence of 37% formaldehyde essentially as described by L. Benoiton, *Can. J. Chem.* 42, 2043 (1969), for the N$^\alpha$-acetyl analog. Purification was achieved by chromatography on silica gel with the solvent system n-BuOH:py:H$_2$O=2:2:1. The yields are 40-65% and the products are amorphous. NMR (CDCl$_3$): 1.41, s, 9H, t-butoxy group; 1.9-1.5, m, 6H, $\beta$, $\gamma$, $\delta$-CH$_2$; 2.6, s, 6H, N(CH$_3$)$_2$; 2.8, m, 2H, $\epsilon$-CH$_2$; 4.03, m, 1H, $\alpha$-CH.

BOC-D-AnGlu. 0.62 g, 3 mmoles, DCC was added to an ice-cooled solution of 1.10 g, 3 mmoles, BOC-D-glutamic acid $\alpha$-benzylester and 0.39 g, 3 mmoles, p-anisidine in 25 ml CH$_2$Cl$_2$. The reaction mixture was stirred while warming up to room temperature and then another 17 h. The dicyclohexylurea was then filtered off and CHCl$_3$ added to a total volume of 125 ml. This solution was extracted with 2×1N H$_2$SO$_4$, H$_2$O, saturated NaHCO$_3$, 2×H$_2$O and dried (MgSO$_4$). Evaporation and recrystallization from EtOH gave 0.99 g, 74% product, m.p. 129.5°-131° C. $R_f$ (4% MeOH in CHCl$_3$)=0.53. This product was dissolved in 30 ml MeOH and 10 ml EtOH and hydrogenated in the presence of 0.3 g Pd/C at 50 psi for 2.5 h. Filtration and evaporation gave a quantitative yield of BOC-D-AnGlu. Not crystalline. Purity >98%. NMR (CDCl$_3$): 1.45, s, 9H, t-butoxy group; 2.35-1.95, m, 2H, $\beta$-CH$_2$; 2.6-2.4, m, 2H, $\gamma$-CH$_2$; 3.76, s, 3H, OCH$_3$; 4.3, m, 1H, $\alpha$-CH; 6.82 and 7.42, broad d, 2H each, aromatic protons.

BOC-Me$_3$Arg. First, N,N,N',S-tetramethylisothiourea was prepared by the procedure of Lecher and Hardy (U.S. No. 2,872,484, Feb. 3, 1959, *Chem. Abstr.* 53, 11238c). B.p. (15 mm)=74° C., lit(above) 68° C. at 11 mm. BOC-Orn, 9 mmoles, and teramethylisothiourea, 10 mmoles, were dissolved in 15 ml DMF and 2 ml triethylamine and incubated at 100° C. for 2 h and at room temperature for 10 h. Then the reaction mixture was evaporated to dryness and passed through a silica gel column eluted by iPrCH:triethylamine:H$_2$O=42:6:13. The white solid so obtained was dissolved in H$_2$O and the solution was acidified with 6N HCl and lyophilized to give 5.5 mmoles product. $R_f$ (column eluant)=0.50. NMR (D$_2$O): 1.42, s, 9H, t-butoxy group, 2.80, m, 1H, $\alpha$-CH; 2.89, s, 3H, CH$_3$ on guanidino group; 2.96, s, 6H, (CH$_3$)$_2$N; 3.25, t, 2H, $\delta$-CH$_2$; 1.50, m, 4H, $\beta$, $\gamma$-CH$_2$.

BOC-Dpo. From 10 mmoles argininehydrochloride and 1.72 g sodium hydrogencarbonate dissolved in 17 ml H$_2$O, 28.6 ml acetylacetone and 28.6 ml EtOH was obtained 7.5 mmoles Dpo following the procedure of F.-S. Tjoeng et al., *Chem. Ber.* 108, 862 (1975). The product was then converted to the corresponding BOC- derivative using di-t-butyl dicarbonate in 50% aqueous dioxane in the presence of sodium hydroxide. This reaction proceeds in essentially quantitative yield. $R_f$(nBuOH:HOAc:H$_2$O=4:1:2)=0.63. NMR (CDCl$_3$): 1.45, s, 9H, t-butoxy group; 1.9-1.5, 4H, $\beta$, $\gamma$-CH$_2$; 2.33, s, 6H, CH$_3$; 3.46, m, 2H, $\delta$-CH$_2$; 4.24, m, 1H, $\alpha$-CH; 6.35, s, 1H, aromatic H. L- and D- forms react similarly.

BOC-D-Et$_2$hArg. This compound was prepared by the method of Nestor and Vickery, U.S. Pat. No. 4,530,920, July 23, 1985. $R_f$ (nBuOH:HOAc:H$_2$O=4:1:2)=0.52.

SYNTHESIS OF THE PEPTIDES

The peptides were synthesized by the solid phase method using a Beckman Model 990 Peptide Synthesizer. The benzhydrylamine hydrochloride resin (BHA-resin) was used as a solid support. The program of the synthesizer was divided into subprograms.

1. Deprotection: 1. CH$_2$Cl$_2$ (2×wash, 1 or 2 min); 2. 50% TFA in CH$_2$Cl$_2$ containing 0.1% indole (1×wash, 1 or 2 min); 3. 50% TFA in CH$_2$Cl$_2$ containing 0.1% indole (deprotection, 20 min); 4. CH$_2$Cl$_2$ (2×wash).

2. Neutralization: 1. CH$_2$Cl$_2$ (2×wash, 1 or 2 min); 2. DIEA (10% in CH$_2$Cl$_2$) (2×wash, 1 or 2 min); 3. DIEA (10% in CH$_2$Cl$_2$) (neutralization, 5 min); 4. CH$_2$Cl$_2$ (2×wash, 1 or 2 min).

3. DCC Coupling: 1. CH$_2$Cl$_2$ (2×wash, 1 or 2 min); 2. amino acid solution in CH$_2$Cl$_2$ (delivery, transfer, mix, 5 min); 3. DCC (10% in CH$_2$Cl$_2$, (delivery and mix, 180 min); 4. CH$_2$Cl$_2$ (2×wash, 1 or 2 min).

4. Active Ester Coupling: not used.

5. Final Wash: 1. CH$_2$Cl$_2$ (2×wash, 1 or 2 min); 2. i-PrOH (3×wash, 1 or 2 min); 3. DMF (3×wash, 1 or 2 min); 4. CH$_2$Cl$_2$ (3×wash, 1 or 2 min).

6. Wash after TFA Treatment: 1. CH$_2$Cl$_2$ (2×wash, 1 or 2 min); 2. i-PrOH (2×wash, 1 or 2 min); CH$_2$Cl$_2$ (3×wash, 1 or 2 min).

7. Acetylation: 1. CH$_2$Cl$_2$ (2×wash, 1 or 2 min); 2. 25% Ac$_2$O and Py in CH$_2$Cl$_2$ (1×wash, 1 or 2 min); 3. 25% Ac$_2$O and Py in CH$_2$Cl$_2$ (acetylation, 20 min); 4. CH$_2$Cl$_2$ (2×wash, 1 or 2 min).

The first amino acid was attached to the resin by the program sequence 2-3-5. Before placing the resin into the reaction vessel, the resin was washed in a separatory funnel with 25 ml CH$_2$Cl$_2$/g resin to remove the fine particles. In all couplings, usually a 3-4 fold excess of the Boc-amino acid over the nitrogen content of the resin was used. This procedure generally resulted in a complete coupling reaction. If a positive ninhydrin color reaction was observed, a second coupling was performed (program sequence 3-5). Then, the resin was acetylated (program sequence 7-5).

The next amino acid was attached by the program sequence 1-6-2-3-5. For DCC coupling, all amino acids were dissolved in CH$_2$Cl$_2$. Acetylation of the amino acid residue in position 1 was performed using the program sequence 1-6-2-7-5. The volume of the solvents and the reagents used for the washing and the performing of the chemical reactions was about 10 ml/g resin.

CLEAVAGE OF THE PEPTIDES FROM THE RESIN

After all of the amino acids had been coupled, the peptide resin was dried overnight, in vacuo, by an oil pump. The resin was then treated with double-distilled liquid hydrogen fluoride (10 ml/g resin) containing 10-25% distilled anisole or p-cresol for 1 hr at 0° C. Then, the HF was evaporated under reduced pressure and the residue was dried overnight, in vacuo, by an oil pump. The mixture was then extracted several times with Et$_2$O (25 ml/g resin), and then with aq. HOAC, 30%, 50%, 10%, and once with 25 ml distilled, deionized water. The combined aqueous solution was lyophilized to yield the crude peptide.

PURIFICATON AND CHARACTERIZATION OF THE PEPTIDES

Most peptides were purified by silica gel chromatography (1×60 cm column) using one of the solvent systems nBuOH:HOAc:$H_2O$=4:1:2 or 4:1:5 upper phase or nBuOAc:nBuOH:HOAc:$H_2O$=2:8:2:3 followed by gelfiltration over Sephadex G 25 with 6% HOAc as the eluant. In the case of unsatisfactory purity after this procedure the peptides were further purified by semi-preparative HPLC using a Waters liquid chromatograph equipped with a 660 solvent programmer. A 1.2×25 cm μ-Bondapak $C_{18}$ column was used with the solvent system A=0.1M $NH_4OAc$ pH 5.0 and B=20% A+80% $CH_3CN$. Different gradients of increasing amounts of B in 15-25 minutes were employed to effect purification.

An alternate purification scheme has been gelfiltration over G 25 with 6% HOAc followed by chromatography over Sephadex LH 20 (2.5×100 cm) with the solvent system $H_2O$:nBuOH:HOAc:MeOH=90:10:10:8. If necessary, the latter procedure was repeated 1-2 times.

The purity of the peptides was assessed by thin layer chromatography on Merck silica gel plates in at least four different solvent systems as shown in Table II. The spots were developed with the chlorine/o-tolidine reagent. In Table II are also shown the conditions and results of analytical HPLC. The equipment was the one described above except that an analytical μ-Bondapak $C_{18}$ column (3.9 mm×30 cm) was used.

Amino acid analyses were performed on a Beckman model 118 CL amino acid analyzer. Samples of about 0.5 mg were hydrolyzed in 6N hydrochloric acid in sealed glass tubes for 24 h at 110° C. The residue was then evaporated and dissolved in citrate buffer, pH 2.2 and applied to the analyzer. The results are in Table III.

BIOASSAYS OF THE PEPTIDES AND DISCUSSION OF DATA

The antiovulatory activity, AOA, in rats was determined as described by Humphries et al., *J. Med. Chem.* 21(1), 120, 1978. The wheal test was performed by intradermally injecting 10 μg of peptide in 100 μl of saline into anaesthesized rats, measuring the ideally circular wheal response and calculating the area. The in vitro histamine release test was done as described by Karten et al., loc. cit. The results of these bioassays are presented in Table I.

Of the 57 peptides in Table I, 21 have an AOA of about 90% or more at a dosage of 1 μg in the present assay. Of the 37 peptides for histamine release in the rat mast cell assay, 10 had $E_D50$ values of 300 or more as compared to 0.17 for the standard compound [N-Ac-D-2-Nal$^1$, D-4-F-Phe$^2$, D-Trp$^3$, D-Arg$^6$]-LHRH. Nine additional analogs had $E_D50$ values ranging from 86 to 288, i.e. they do not release more histamine than clinically used "superagonists".

Of the 37 peptides tested in the rat mast cell assay, seven (No's 4, 23, 24, 43, 44, 53, 55) had both an AOA of 90% or more at 1 μg and an $E_D50$ value of >86 μg/ml. This includes the most potent analog, No. 53, which has 100% AOA at 0.5 μg and 40% AOA at 0.25 μg. The $E_D50$ value for this analog is 93±28. It has thus been possible to efficiently combine high AOA with low histamine release.

Structural features in common for these seven peptides are: (1) A D-Lys residue in position 6 acylated by the weakly basic nicotinic acid or analogs like picolinic and 6-methylnicotinic acid. (2) The corresponding acylated L-Lys residue or the natural Tyr in position 5. (3) The alkylated derivatives ILys or IOrn in position 8. (4) Arg is absent from the sequence.

Two examples of the influence of Arg on histamine release are the pairs 43,10 and 4,1. No. 43 has the sequence N-Ac-D-2-Nal, D-pClPhe, D-3-Pal, Ser, NicLys, D-NicLys, Leu, ILys, Pro, D-Ala-$NH_2$. Its $E_D50$ value is >300. No. 10 is identical in sequence except that NicLys$^5$ is replaced by Arg$^5$. This caused the $E_D50$ value to decrease to 4.3±0.52. No. 4 has identical sequence as No. 43 except for Tyr in position 5. Its ED50 value is 133±22. In No. 1, ILys$^8$ in this sequence is replaced by Arg$^8$ which caused the $E_D50$ value to decrease to 39.2±7. It thus seems that position 5 is more sensitive than position 8 for Arg substitution.

In position 8, the alkylated ILys and IOrn residues are superior to Lys and Orn, respectively, both with respect to AOA and histamine release (pairs 3,4 and 6,7). Whether ILys$^8$ or IOrn$^8$ is best seems to be sequence dependent.

TABLE I

ANTAGONISTS OF LHRH BASED UPON
[()$^1$,D-pClPhe$^2$,()$^3$,Ser$^4$,()$^5$,()$^6$,Leu$^7$,()$^8$,Pro$^9$,D-Ala$^{10}$]-$NH_2$

| NO. | ()$^1$ | ()$^3$ | ()$^5$ | ()$^6$ | ()$^8$ | AOA %/μg 0.5 | 1.0 | 2.0 | Wheal Area mm$^2$/10 μg | $E_D50$ μg/ml |
|---|---|---|---|---|---|---|---|---|---|---|
| ANALOGS WITH D-NICLYS IN POSITION 6 |||||||||||
| 1. | N—Ac-D-2-Nal | D-3-Pal | Tyr | D-NicLys | Arg | 60 | 100 | — | 85 | 39.2 ± 7 |
| 2. | " | " | " | " | Me$_3$Arg | — | — | — | | 39.9 ± 7 |
| 3. | " | " | " | " | Lys | — | 27 | — | 119.5 ± 3.2 | |
| 4. | " | " | " | " | ILys | 45 | 89 | 100 | 79.0 ± 9.2 | 133 ± 22 |
| 5. | " | " | " | " | Me$_2$Lys | — | 90 | 100 | 122.7 | 18.4 |
| 6. | " | " | " | " | Orn | — | — | 67 | 129.4 ± 3.3 | 19.3 |
| 7. | " | " | " | " | IOrn | 22 | 71 | — | 92.2 ± 2.9 | >300 |
| 8. | " | " | Arg | " | Arg | 0 | 42 | — | 146.8 | |
| 9. | " | D-Tyr | " | " | " | 33 | — | — | 113.2 ± 5.6 | 1.73 |
| 10. | " | D-3-Pal | " | " | ILys | 43 | 17 | — | 196.9 ± 4.2 | 4.3 ± 0.52 |
| 11. | " | " | Me$_3$Arg | " | " | — | — | 44 | 140 ± 7.0 | |
| 12. | " | " | Dpo | " | " | 56 | — | — | 110 ± 3 | |
| 13. | " | " | ILys | " | " | — | 89 | — | 132.7 ± 0 | 20.3 |
| 14. | " | " | His | " | Arg | — | 89 | — | 139.7 ± 0 | |
| 15. | " | " | 3-Pal | " | " | — | 100 | — | 146.4 ± 3.6 | |
| 16. | " | " | " | " | ILys | — | 75 | — | 132.8 ± 6.0 | 86 ± 28* |
| 17. | " | " | " | " | IOrn | — | 100 | — | 139.9 ± 7.2 | 55 ± 13* |
| 18. | " | " | Ile | " | ILys | — | 82 | — | 147.7 ± 7.1 | 324 ± 20 |

TABLE I-continued

| No. | ( )¹ | ( )³ | ( )⁵ | ( )⁶ | ( )⁸ | 0.25 | 0.5 | 1.0 | Wheel Area mm²10UG | $E_D50$ UG/ML |
|---|---|---|---|---|---|---|---|---|---|---|
| 19. | " | " | " | " | IOrn | — | 55 | — | 116.5 ± 8.7 | 151 ± 75 |
| 20. | " | " | NicOrn | " | " | — | 73 | — | 113.6 ± 10.9 | 57 ± 13 |
| 21. | " | " | DMGlys | " | ILys | 20 | — | — | 110 ± 3 | 34 ± 1.1 |
| 22. | " | " | PicLys | " | " | 64 | 100 | — | 116 ± 3.3 | 39 ± 1.0 |
| 23. | N—Ac-D-pClPhe | " | Tyr | " | " | — | 100 | — | 139.9 ± 7.2 | 198 ± 33* |
| 24. | N—Ac-D-Cl₂Phe | " | " | " | " | 0 | 89 | — | 103.9 ± 5.3 | 311 ± 65* |

ANALOGS WITH NICYLS IN POSITION 5

| 25. | N—Ac-D-2-Nal | D-3-Pal | NicLys | D-3-Pal | Arg | 0 | — | — | 112 | |
| 26. | " | " | " | D-His | " | — | 100 | — | 146.7 ± 3.6 | |
| 27. | " | " | " | D-ILys | " | — | 56 | 73 | 196.9 ± 4.1 | |
| 28. | " | " | " | D-Dpo | ILys | 40 | 100 | — | 165.2 ± 6.7 | 6.7 ± 2.2 |
| 29. | " | " | " | D-BzLys | " | — | 50 | — | 119.6 ± 6.7 | >300 |
| 30. | " | " | " | D-Et₂hArg | " | — | 67 | — | 123 ± 5.8 | |
| 31. | " | " | " | D-PucLys | " | 36 | — | — | 120 ± 7 | 60 ± 1.4 |
| 32. | " | " | " | D-AnGlu | " | — | 67 | — | 113 ± 7 | >300 |
| 33. | " | " | " | trans-D-NACAla | " | — | 70 | — | 119.5 ± 3.2 | |
| 34. | " | " | " | cis-D-NACAla | " | — | 100 | — | 113.6 ± 10.9 | 37 ± 1.1 |
| 35. | " | " | " | D-Me₂Lys | " | — | 82 | — | 111 ± 2 | 262 ± 23 |
| 36. | " | " | " | D-PzcLys | " | — | — | — | 122.2 ± 5.1 | |

ANALOGS WITH NICLYS IN POSITION 8

| 37. | N—Ac-D-2-Nal | D-3-Pal | Tyr | D-Arg | NicLys | — | — | 88 | 136.6 ± 6.8 | 14.2 |
| 38. | " | " | Arg | D-3-Pal | " | 0 | — | — | 99.0 ± 10.3 | |
| 39. | " | " | Tyr | D-ILys | " | — | — | 100 | 122.8 ± 5.8 | |

ANALOGS WITH NICLYS AND D-NICLYS
in POSITIONS 5, 6 or in POSITION 8, 6 or in POSITION 3, 6

| 40. | N—Ac-D-2-Nal | D-3-Pal | NicLys | D-NicLys | Arg | 22 | 100 | — | 126.2 ± 8.8 | |
| 41. | " | " | " | " | Me₃Arg | — | — | 100 | 150.9 ± 14.0 | |
| 42. | " | " | " | " | Dpo | — | 18 | — | 113.6 ± 11.1 | <300 |
| 43. | " | " | " | " | ILys | 36 | 100 | 100 | 132.7 ± 0 | 300 |
| 44. | " | " | " | " | IOrn | 88 | 100 | — | 136.0 ± 3.4 | 206 ± 64 |
| 45. | " | " | " | " | CypLys | — | 64 | — | 147.0 ± 7.2 | 171 ± 49 |
| 46. | " | " | Tyr | " | NicLys | — | 0 | — | 82.6 ± 2.8 | 300 |
| 47. | " | " | His | " | " | — | — | 18 | 136.3 ± 6.8 | |
| 48. | " | " | ILys | " | " | — | 30 | — | 132.8 ± 5.9 | |
| 49. | " | D-NicLys | Tyr | " | Arg | — | 89 | — | 101.0 ± 6.0 | |

| No. | ( )¹ | ( )³ | ( )⁵ | ( )⁶ | ( )⁸ | 0.25 | 0.5 | 1.0 | 2.0 | 10.0 | Wheel Area mm²10UG | $E_D50$ UG/ML |
|---|---|---|---|---|---|---|---|---|---|---|---|---|

MISCELLANEOUS ANALOGS

| 50. | N—Ac-D-2-Nal | D-3-Pal | NicLys | D-NicLys | NicLys | — | — | 0 | — | — | 122.8 ± 5.7 | |
| 51. | " | " | " | NicLys | ILys | — | — | — | — | 8 | 123 ± 5.9 | >300 |
| 52. | " | " | INicLys | D-INicLys | " | — | 63 | 91 | — | — | 140.3 ± 13.9 | 15 ± 8.2 |
| 53. | " | " | PicLys | D-PicLys | " | 40 | 100 | 90 | — | — | 123.0 ± 0.0 | 93 ± 28 |
| 54. | " | " | Arg | D-BzLys | " | — | — | 63 | — | — | 169.0 ± 7.7 | 8.7 ± 3* |
| 55. | " | " | NNicLys | D-MNicLys | " | — | 56 | 100 | — | — | 126.1 ± 6.7 | >300 |
| 56. | " | " | DMGLys | D-BzLys | " | — | — | 100 | — | — | 136.6 ± 6.7 | 24 ± 0.3 |
| 57. | " | " | PzcLys | D-PzcLys | " | — | — | — | — | — | 110.2 ± 8.1 | 288 ± 30 |

*In this test series the standard compound had an $E_D50$ value of 0.46 instead of the usual 0.1–0.2.

ABBREVIATIONS
AnGlu = 4-(4-methoxyphenylcarbamoyl)-2-aminobutyric acid
BzLys = N^ε-benzoyllysine
Cl₂Phe = 3.4-dichlorophenylalanine
CypLys = N^ε-cyclopentyllysine
DMGLys = N^ε-(N,N-dimethylglycyl)lysine
Dpo = N^δ-(4,6-dimethyl-2-pyrimidyl) ornithine
Et₂hArg = $N^G,N^G$-diethylhomoarginine
ILys = N^ε-isopropyllysine
INicLys = N^ε-isonicotinoyllysine
IOrn = N^δ-isopropylornithine
Me₃Arg = $N^G,N^G,N^{G1}$-trimethylarginine
Me₂Lys = N^ε,N^ε-dimethyllysine
MNicLys = N^ε-(6-methylnicotinoyl)lysine
2-Nal = 3-(2-naphthyl)alanine
NicLys = N^ε-nicotinoyllysine
NicOrn = N^δ-nicotinoylornithine
3-Pal = 3-(3-pyridyl)alanine
pClPhe = 4-chlorophenylalanine
PicLys = N^ε-picoloyllysine
NACAla = 3(4-nicotinoylaminocyclohexyl)alanine
PzcLys = N^ε-pyrazinylcarbonyllysine

TABLE II

CHROMATOGRAPHIC DATA ON THE LHRH ANTAGONISTS

| No. | Linear Gradient % Change of CH₃CN | HPLC Retention Time (min) | Rf₁ | Rf₂ | Rf₃ | Rf₄ | Rf₅ | Rf₆ | Rf₇ | Rf₈ | Rf₉ | Rf₁₀ |
|---|---|---|---|---|---|---|---|---|---|---|---|---|
| 1. | 40 to 100 | 6.7 | — | 0.25 | — | 0.27 | — | — | 0.75 | 0.77 | 0.48 | — |
| 2. | 24 to 80 | 7.6 | — | 0.11 | 0.34 | — | — | — | 0.83 | 0.62 | 0.03 | — |
| 3. | 24 to 80 | 7.3 | — | 0.16 | 0.38 | — | — | — | 0.82 | 0.67 | 0.05 | — |
| 4. | 16 to 64 | 10.4 | — | 0.16 | 0.36 | — | — | — | 0.73 | 0.67 | 0.09 | — |

TABLE II-continued
CHROMATOGRAPHIC DATA ON THE LHRH ANTAGONISTS

| No. | Linear Gradient % Change of $CH_3CN$ | HPLC Retention Time (min) | TLC | | | | | | | | | |
|---|---|---|---|---|---|---|---|---|---|---|---|---|
| | | | $Rf_1$ | $Rf_2$ | $Rf_3$ | $Rf_4$ | $Rf_5$ | $Rf_6$ | $Rf_7$ | $Rf_8$ | $Rf_9$ | $Rf_{10}$ |
| 5. | 16 to 64 | 10.1 | — | 0.10 | 0.31 | — | — | — | 0.63 | 0.49 | 0.05 | — |
| 6. | 24 to 80 | 7.0 | — | 0.25 | 0.42 | 0.30 | — | — | 0.76 | 0.75 | — | — |
| 7. | 24 to 80 | 7.6 | — | 0.23 | 0.42 | 0.27 | — | — | 0.77 | 0.74 | — | — |
| 8. | 32 to 80 | 3.8 | — | 0.14 | 0.38 | 0.27 | — | — | 0.62 | 0.63 | 0.05 | — |
| 9. | 24 to 80 | 7.0 | 0.46 | 0.36 | 0.40 | 0.40 | 0.74 | — | 0.82 | 0.81 | — | — |
| 10. | 24 to 80 | 6.3 | 0.44 | — | 0.38 | — | — | 0.66 | 0.64 | — | — | — |
| 11. | 24 to 80 | 6.2 | — | — | 0.28 | 0.19 | — | 0.01 | 0.85 | 0.14 | — | 0.46 |
| 12. | 24 to 80 | 7.2 | 0.45 | — | 0.38 | — | — | 0.76 | 0.72 | — | — | — |
| 13. | 24 to 80 | 6.0 | 0.46 | 0.09 | 0.41 | 0.33 | — | — | 0.63 | — | — | 0.59 |
| 14. | 32 to 80 | 4.2 | — | 0.12 | 0.44 | 0.26 | — | — | 0.74 | 0.54 | 0.05 | — |
| 15. | 32 to 80 | 3.9 | — | 0.12 | 0.38 | 0.17 | — | — | 0.79 | 0.40 | 0.24 | — |
| 16. | 24 to 80 | 7.2 | 0.45 | — | 0.41 | — | — | 0.75 | 0.69 | — | — | 0.54 |
| 17. | 24 to 80 | 7.2 | 0.46 | — | 0.38 | — | — | 0.76 | 0.71 | — | — | 0.56 |
| 18. | 28 to 80 | 7.7 | 0.51 | — | 0.37 | — | — | 0.77 | 0.71 | 0.63 | — | — |
| 19. | 28 to 80 | 7.5 | 0.51 | — | 0.37 | — | — | 0.78 | 0.72 | 0.63 | — | — |
| 20. | 24 to 72 | 7.2 | 0.48 | — | 0.33 | — | — | 0.72 | 0.66 | 0.59 | — | — |
| 21. | 16 to 64 | 9.1 | — | — | 0.28 | — | 0.71 | — | — | 0.07 | — | 0.17 |
| 22. | 16 to 64 | 11.2 | — | — | 0.34 | — | 0.87 | — | 0.65 | — | — | 0.55 |
| 23. | 40 to 80 | 10.7 | — | 0.23 | 0.43 | — | — | — | 0.79 | 0.71 | — | — |
| 24. | 40 to 80 | 11.2 | — | 0.24 | 0.39 | — | — | — | 0.76 | 0.73 | — | — |
| 25. | 32 to 80 | 5.7 | — | 0.08 | — | 0.19 | — | — | 0.68 | 0.48 | 0.15 | — |
| 26. | 32 to 80 | 3.4 | — | 0.11 | 0.41 | 0.25 | — | — | 0.72 | 0.46 | 0.05 | — |
| 27. | 20 to 80 | 6.4 | — | 0.08 | 0.32 | — | — | — | 0.80 | 0.55 | 0.03 | — |
| 28. | 24 to 80 | 7.0 | 0.47 | — | 0.39 | — | — | 0.77 | 0.73 | — | — | — |
| 29. | 24 to 72 | 8.5 | 0.51 | — | 0.36 | — | — | 0.78 | 0.72 | 0.66 | — | — |
| 30. | 24 to 80 | 6.9 | 0.44 | — | 0.38 | — | — | 0.69 | 0.67 | — | — | — |
| 31. | 16 to 64 | 11.0 | — | — | 0.32 | — | 0.92 | — | 0.68 | — | — | 0.55 |
| 32. | 16 to 64 | 11.3 | — | — | 0.35 | — | 0.93 | — | 0.71 | — | — | 0.56 |
| 33. | — | — | — | — | 0.38 | — | 0.86 | — | 0.67 | — | — | 0.47 |
| 34. | — | — | — | — | 0.38 | — | 0.87 | — | 0.65 | — | — | 0.51 |
| 35. | — | — | — | — | 0.39 | — | — | 0.79 | 0.78 | — | — | 0.64 |
| 36. | — | — | 0.50 | — | 0.41 | — | — | 0.78 | 0.78 | — | — | 0.65 |
| 37. | 24 to 80 | 6.9 | — | — | 0.26 | 0.44 | 0.32 | — | 0.76 | 0.78 | — | — |
| 38. | 32 to 80 | 4.1 | | 0.14 | — | 0.28 | | | 0.65 | 0.61 | 0.27 | — |
| 39. | 24 to 80 | 8.0 | — | 0.17 | 0.38 | — | — | — | 0.87 | 0.68 | 0.08 | — |
| 40. | 32 to 80 | 4.4 | — | 0.13 | 0.38 | 0.21 | — | — | 0.81 | 0.68 | 0.20 | — |
| 41. | 24 to 80 | 8.2 | — | 0.07 | 0.31 | — | — | — | 0.87 | 0.44 | 0.03 | — |
| 42. | 28 to 80 | 7.4 | 0.51 | — | 0.38 | — | — | 0.81 | 0.73 | 0.62 | — | — |
| 43. | 24 to 80 | 7.3 | 0.49 | 0.14 | 0.43 | 0.36 | — | — | 0.71 | 0.67 | — | — |
| 44. | 24 to 80 | 7.5 | — | 0.11 | 0.35 | — | — | — | 0.85 | 0.64 | 0.04 | — |
| 45. | 24 to 72 | 7.8 | 0.52 | — | 0.39 | — | — | 0.78 | 0.73 | 0.63 | — | — |
| 46. | 24 to 80 | 7.7 | 0.53 | 0.02 | 0.51 | 0.47 | — | — | 0.83 | — | — | — |
| 47. | 24 to 80 | 7.0 | 0.53 | 0.14 | 0.45 | 0.39 | — | — | 0.73 | 0.69 | — | — |
| 48. | 24 to 80 | 7.0 | 0.53 | 0.16 | 0.46 | 0.36 | — | — | 0.76 | 0.68 | — | — |
| 49. | 16 to 64 | 10.7 | — | 0.35 | 0.43 | — | — | — | 0.75 | 0.71 | 0.12 | — |
| 50. | 16 to 64 | 10.9 | — | 0.17 | 0.38 | — | — | — | 0.72 | 0.66 | 0.17 | — |
| 51. | 24 to 80 | 7.3 | — | 0.10 | 0.36 | — | — | — | 0.85 | 0.64 | 0.04 | — |
| 52. | 24 to 72 | 7.0 | 0.47 | — | 0.36 | — | — | 0.70 | 0.65 | 0.60 | — | — |
| 53. | 24 to 72 | 8.9 | 0.50 | — | 0.32 | — | — | 0.78 | 0.73 | 0.62 | — | — |
| 54. | 16 to 64 | 8.2 | — | — | 0.33 | — | 0.86 | — | — | 0.59 | — | 0.52 |
| 55. | 16 to 64 | 7.9 | — | — | 0.31 | — | 0.86 | — | 0.65 | — | — | 0.55 |
| 56. | 16 to 64 | 10.3 | — | — | 0.29 | — | 0.75 | — | — | 0.16 | — | 0.35 |
| 57. | — | — | 0.46 | — | 0.39 | — | — | 0.77 | 0.73 | — | — | 0.61 |

HPLC Solvent System
Buffer A = 0.01 M $KH_2PO_4$, pH = 3
Buffer B = 20% A in $CH_3CN$
Elution is performed using a linear gradient at various percentages of $CH_3CN$ in 15 min at a flow rate of 2 ml per minute
TLC Solvents
$Rf_1$ = nBuOH:pyridine:HOAc:$H_2O$ = 40:1:10:20
$Rf_2$ = nBuOAc:nBuOH:HOAc:$H_2O$ = 2:8:2:3
$Rf_3$ = nBuOH:HOAc:$H_2O$ = 4:1:2
$Rf_4$ = nBuOH:HOAc:$H_2O$ = 4:1:5 (upper)
$Rf_5$ = EtOAC:pyridine:HOAc:$H_2O$ = 5:5:1:3
$Rf_6$ = nBuOH:pyridine:HOAc:$H_2O$ = 5:3.3:1:4
$Rf_7$ = nBuOH:pyridine:HOAc:$H_2O$ = 4:1:1:2
$Rf_8$ = EtOAC:nBuOH:HOAc:$H_2O$ = 1:1:1:1
$Rf_9$ = EtOAc:pyridine:HOAc:$H_2O$ = 20:5:3:3
$Rf_{10}$ = nBuOH:pyridine:HOAc:$H_2O$ = 30:10:3:12

TABLE III
AMINO ACID ANALYTICAL DATA FOR THE LHRH ANTAGONISTS

| No. | Ser | Tyr | Arg | Leu | Pro | Ala | Lys | His | Ile | 2-Nal | pClPhe | 3-Pal | ILys | Others |
|---|---|---|---|---|---|---|---|---|---|---|---|---|---|---|
| 1. | 0.914 | 1.02 | 1.01 | 1.02 | 1.00 | 1.01 | 1.03 | — | — | + | + | + | — | — |
| 2. | 0.91 | 0.95 | — | 1.01 | 1.16 | 0.95 | 1.01 | — | — | + | + | 1.02 | — | $Me_3Arg$ (+) |
| 3. | 0.77 | 0.96 | — | 0.98 | 1.08 | 0.90 | 2.22 | — | — | + | + | 1.08 | — | — |

TABLE III-continued
AMINO ACID ANALYTICAL DATA FOR THE LHRH ANTAGONISTS

| No. | Ser | Tyr | Arg | Leu | Pro | Ala | Lys | His | Ile | 2-Nal | pClPhe | 3-Pal | ILys | Others |
|---|---|---|---|---|---|---|---|---|---|---|---|---|---|---|
| 4. | 0.83 | 1.20 | — | 1.01 | 0.92 | 0.92 | 1.07 | — | — | + | + | 1.06 | + | — |
| 5. | 0.89 | 0.98 | — | 1.01 | 0.95 | 0.97 | 1.22 | — | — | + | + | 0.98 | — | Me$_2$Lys (+) |
| 6. | 0.94 | 0.78 | — | 1.07 | 0.98 | 1.14 | + | — | — | + | + | 1.08 | — | Orn (+) |
| 7. | 0.88 | 0.98 | — | 1.03 | 1.00 | 1.01 | 1.04 | — | — | + | + | 1.06 | — | IOrn (+) |
| 8. | 0.86 | — | 2.21 | 1.01 | 0.87 | 0.92 | 1.13 | — | — | + | + | + | — | — |
| 9. | 0.78 | 1.13 | 2.03 | 0.97 | 0.74 | 1.29 | 1.06 | — | — | + | + | — | — | — |
| 10. | 0.93 | — | 0.98 | 1.04 | 1.02 | 1.03 | 1.00 | — | — | + | + | 0.99 | + | — |
| 11. | 0.90 | — | — | 1.03 | 1.03 | 1.03 | 0.99 | — | — | + | + | 1.03 | + | Me$_3$Arg (+) |
| 12. | 0.86 | — | — | 1.00 | 1.13 | 1.01 | + | — | — | + | + | + | + | Dpo (+) |
| 13. | 0.94 | — | — | 1.04 | 1.00 | 0.94 | 1.04 | — | — | + | + | 1.05 | ++ | — |
| 14. | 0.97 | 1.01 | 1.01 | 1.04 | 1.02 | 1.03 | 1.00 | 0.93 | — | + | + | 1.00 | — | — |
| 15. | 0.92 | 1.00 | 1.00 | 1.01 | 0.96 | 1.01 | 1.03 | — | — | + | + | 2.04 | — | — |
| 16. | 0.80 | — | — | 1.02 | 0.99 | 1.19 | 1.03 | — | — | + | + | 1.98 | + | — |
| 17. | 0.84 | — | — | 1.05 | 1.02 | 1.03 | 1.04 | — | — | + | + | 2.02 | — | IOrn (+) |
| 18. | 0.95 | — | — | 1.05 | 1.04 | 1.07 | 0.97 | — | 0.92 | + | + | 0.99 | + | — |
| 19. | 0.97 | — | — | 1.10 | 1.05 | 1.09 | 0.93 | — | 0.89 | + | + | 0.97 | — | IOrn (+) |
| 20. | 0.91 | — | — | 0.97 | 0.90 | 0.96 | 1.33 | — | — | + | + | 0.93 | — | Orn (+), IOrn (+) |
| 21. | 1.01 | — | — | 0.99 | 0.96 | 1.00 | 2.01 | — | — | + | + | 1.02 | + | — |
| 22. | 0.87 | — | — | 0.98 | 0.96 | 0.96 | 2.15 | — | — | + | + | 1.07 | + | — |
| 23. | 1.01 | 0.89 | — | 1.04 | 1.02 | 1.08 | 0.97 | — | — | — | ++ | 1.00 | + | — |
| 24. | 0.99 | 0.91 | — | 1.04 | 1.01 | 1.04 | 0.99 | — | — | — | + | 1.02 | + | 3,3-Cl$_2$Phe |
| 25. | 0.91 | — | 0.89 | 1.00 | 1.17 | 1.01 | 1.02 | — | — | + | + | ++ | — | — |
| 26. | 0.98 | — | 0.99 | 1.03 | 0.98 | 1.01 | 1.02 | 0.98 | — | + | + | 1.00 | — | — |
| 27. | 0.89 | — | 1.01 | 1.03 | 0.99 | 1.01 | 1.04 | — | — | + | + | 1.04 | + | — |
| 28. | 1.04 | — | — | 1.12 | 1.12 | 1.12 | 0.63 | — | — | + | + | 0.97 | + | Dpo (+) |
| 29. | 0.93 | — | — | 1.03 | 1.04 | 1.03 | 1.97 | — | — | + | + | 1.00 | + | — |
| 30. | 0.99 | — | — | 1.02 | 1.00 | 1.03 | 1.00 | — | — | + | + | 0.96 | + | Et$_2$hArg (+) |
| 31. | 0.94 | — | — | 1.02 | 1.04 | 1.02 | 1.94 | — | — | + | + | 1.03 | + | — |
| 32. | 0.93 | — | — | 1.01 | 0.99 | 1.00 | 1.01 | — | — | + | + | 1.06 | + | Glu 1.00 |
| 33. | 0.91 | — | — | 1.02 | 1.02 | 0.98 | 1.04 | — | — | + | + | 1.04 | + | t-ACAla (+) |
| 34. | 0.93 | — | — | 0.98 | 1.02 | 0.99 | 1.04 | — | — | + | + | 1.07 | + | c-ACAla (+) |
| 35. | 0.94 | — | — | 1.00 | 1.00 | 0.98 | + | — | — | + | + | 1.08 | + | Me$_2$Lys (+) |
| 36. | 0.86 | — | — | 1.00 | 1.04 | 0.99 | 2.06 | — | — | + | + | 1.11 | + | — |
| 37. | 0.89 | 0.98 | 1.00 | 1.02 | 1.01 | 1.01 | 1.05 | — | — | + | + | 1.07 | — | — |
| 38. | 0.83 | — | 1.01 | 1.03 | 1.10 | 0.97 | 1.06 | — | — | + | + | ++ | — | — |
| 39. | 0.82 | 0.95 | — | 1.02 | 1.13 | 0.93 | 1.04 | — | — | + | + | 1.11 | + | — |
| 40. | 0.91 | — | 1.01 | 1.02 | 0.96 | 0.99 | 2.08 | — | — | + | + | 1.03 | — | — |
| 41. | 0.87 | — | — | 1.03 | 0.97 | 0.98 | 2.01 | — | — | + | + | 1.05 | — | Me$_3$Arg (+) |
| 42. | 0.90 | — | — | 1.03 | 1.07 | 1.00 | 2.03 | — | — | + | + | — | — | Dpo (+) |
| 43. | 0.91 | — | — | 1.03 | 1.05 | 0.99 | 2.02 | — | — | + | + | 1.01 | + | — |
| 44. | 0.92 | — | — | 1.02 | 1.05 | 1.01 | 2.03 | — | — | + | + | 0.96 | — | IOrn (+) |
| 45. | 0.82 | — | — | 0.99 | 1.04 | 0.97 | 2.04 | — | — | + | + | 1.10 | — | CypLys (+) |
| 46. | 0.93 | 0.99 | — | 1.02 | 1.04 | 0.98 | 2.02 | — | — | + | + | 1.02 | — | — |
| 47. | 0.97 | — | — | 1.03 | 0.97 | 0.94 | 2.07 | 0.98 | — | + | + | 1.03 | — | — |
| 48. | 0.90 | — | — | 1.02 | 1.01 | 1.00 | 2.03 | — | — | + | + | 1.03 | + | — |
| 49. | 0.90 | 0.99 | 1.00 | 1.03 | 1.01 | 0.99 | 2.07 | — | — | + | + | — | — | — |
| 50. | 0.89 | — | — | 1.01 | 0.98 | 0.98 | 3.02 | — | — | + | + | 1.02 | — | — |
| 51. | 0.91 | — | — | 1.03 | 0.99 | 1.01 | 2.06 | — | — | + | + | 1.01 | + | — |
| 52. | 0.88 | — | — | 0.99 | 1.07 | 0.95 | 2.01 | — | — | + | + | 1.11 | + | — |
| 53. | 0.94 | — | — | 0.99 | 0.97 | 1.08 | 1.95 | — | — | + | + | 1.07 | + | — |
| 54. | 0.92 | — | 1.01 | 1.04 | 1.00 | 1.02 | 1.00 | — | — | + | + | 1.02 | + | — |
| 55. | 0.91 | — | — | 1.04 | 1.00 | 0.99 | 2.05 | — | — | + | + | 1.00 | + | — |
| 56. | 1.01 | — | — | 0.98 | 0.96 | 1.02 | 2.01 | — | — | + | + | 1.00 | + | — |
| 57. | 0.95 | — | — | 0.99 | 1.03 | 0.98 | 2.00 | — | — | + | + | 1.04 | + | — |

*ACAla = 3(4-aminocyclohexyl)alanine

What is claimed:

1. [N-Ac-D-2-Nal$^1$, D-pClPhe$^2$, D-3-Pal$^3$, NicLys$^5$, D-NicLys$^6$, ILys$^8$, D-Ala$^{10}$]-LHRH.

2. [N-Ac-D-2-Nal$^1$, D-pClPhe$^2$, D-3-Pal$^3$, PicLys$^5$, D-PicLys$^6$, ILys$^8$, D-Ala$^{10}$]-LHRH.

3. [N-Ac-D-2-Nal$^1$, D-pClPhe$^2$, D-3-Pal$^3$, NicLys$^5$, D-NicLys$^6$, IOrn$^8$, D-Ala$^{10}$]-LHRH.

4. [N-Ac-D-2-Nal$^1$, D-pClPhe$^2$, D-3-Pal$^3$, PicLys$^5$, D-PicLys$^6$, IOrn$^8$, D-Ala$^{10}$]-LHRH.

5. [N-Ac-D-2-Nal$^1$, D-pClPhe$^2$, D-3-Pal$^3$, MNicLys$^5$, D-MNicLys$^6$, ILys$^8$, D-Ala$^{10}$]-LHRH.

6. [N-Ac-D-2-Nal$^1$, D-pClPhe$^2$, D-3-Pal$^3$, PzcLys$^5$, D-PzcLys$^6$, ILys$^8$, D-Ala$^{10}$]-LHRH.

* * * * *

UNITED STATES PATENT AND TRADEMARK OFFICE
CERTIFICATE OF CORRECTION

PATENT NO. : 4,935,491
DATED : June 19, 1990
INVENTOR(S) : Karl Folkers et al

It is certified that error appears in the above-indentified patent and that said Letters Patent is hereby corrected as shown below:

In column 1, line 1, insert the following sentence:

--The United States Government has rights in this patent as research relating to the invention was partially supported by National Institutes of Health Grant No. HD42381-B.--

Signed and Sealed this

Third Day of October, 1995

Attest:

BRUCE LEHMAN

Attesting Officer     Commissioner of Patents and Trademarks